United States Patent
Ehnholm et al.

(10) Patent No.: US 6,975,896 B2
(45) Date of Patent: Dec. 13, 2005

(54) FIDUCIAL MARKERS FOR MRI

(75) Inventors: Gösta J. Ehnholm, Helsinki (FI); Erkki T. Vahala, Hyvinkaa (FI); Mika P. Ylihautala, Vantaa (FI)

(73) Assignee: Koninklijke Philips Electronics N.V., Eindhoven (NL)

(*) Notice: Subject to any disclaimer, the term of this patent is extended or adjusted under 35 U.S.C. 154(b) by 388 days.

(21) Appl. No.: 10/153,940

(22) Filed: May 23, 2002

(65) Prior Publication Data

US 2003/0220559 A1    Nov. 27, 2003

(51) Int. Cl.⁷ ............................................. A61B 5/05
(52) U.S. Cl. ................ 600/414; 600/417; 600/420
(58) Field of Search .................. 600/426, 414, 600/420; 427/429

(56) References Cited

U.S. PATENT DOCUMENTS

| | | | |
|---|---|---|---|
| 212,323 A * | 2/1879 | Petersson et al. | 56/300 |
| 5,271,400 A * | 12/1993 | Dumoulin et al. | 600/410 |
| 5,362,478 A * | 11/1994 | Desai et al. | 424/9.322 |
| 5,690,908 A | 11/1997 | Deutsch et al. | 424/9.32 |
| 5,729,129 A * | 3/1998 | Acker | 324/207.12 |
| 5,782,764 A | 7/1998 | Werne | 600/411 |
| 5,847,206 A | 12/1998 | Pavia et al. | 562/575 |
| 6,315,981 B1 * | 11/2001 | Unger | 424/9.323 |
| 6,574,497 B1 | 6/2003 | Pacetti | 600/420 |
| 6,628,982 B1 * | 9/2003 | Thomas et al. | 600/431 |
| 2001/0032649 A1 | 10/2001 | Nagano | 128/897 |

FOREIGN PATENT DOCUMENTS

| | | |
|---|---|---|
| JP | 2000-237161 | 9/2000 |
| WO | WO 94/17733 | 8/1994 |

OTHER PUBLICATIONS

Paul Alexander Crandell, "An Accurate Frequency Measuring Technique Using Paramagnetic Resonance Phenomena In The X-Band Region" Wescon /58 Conference Record vol. 2, Aug. 1958.*

* cited by examiner

Primary Examiner—Brian L. Casler
Assistant Examiner—Julianne M. Sullivan
(74) Attorney, Agent, or Firm—Fay, Shrpe, Fagan, Minnich & McKee

(57) ABSTRACT

Fiducials (50) are disposed in an imaging region (14) along with a subject. The fiducials are mounted either to the subject itself, a surgical tool (52), an imaging probe or receive coil (80), or the like. The fiducials are filled with a liquid or gel of a fluorine 19 ($Fl^{19}$) compound which has a resonance frequency that is only 6% off from the resonance frequency of protons. This enables a common transmitter (22), transmit and receive coils, and receiver (34) to be utilized for both proton and fluorine 19 imaging. The proton and fluorine resonance signals are separately reconstructed into corresponding image memories (42, 64). From the positions of the fiducials, a position calculator (66) determines the position of a fiducial carrying surgical tool or probe relative to the proton image. A depiction of the tool or probe from a look-up table (70) is appropriately positioned and rotated (68) and superimposed on the proton image by a video processor (44).

11 Claims, 3 Drawing Sheets

FIDUCIAL MARKERS FOR MRI

BACKGROUND OF THE INVENTION

The present invention relates to the magnetic resonance imaging arts. It finds particular application in conjunction with imaging as a guide for other, possibly invasive, procedures and will be described with particular reference thereto. It is to be appreciated, however, that the present invention may also find application in other procedures in which it is advantageous to determine the location of portions of the patient's anatomy, diagnostic or surgical instruments, and the like, relative to reconstructed images and each other, and is not limited to the aforementioned application.

In magnetic resonance imaging, a substantially uniform main magnetic field is generated within an examination region. The main magnetic field polarizes the nuclear spin system of a patient being imaged within the examination region. Magnetic resonance is excited in dipoles which align with the main magnetic field by transmitting radio frequency excitation signals into the examination region. Specifically, radio frequency pulses transmitted via a radio frequency coil assembly tip the dipoles out of alignment with the main magnetic field and cause a macroscopic magnetic moment vector to precess around an axis parallel to the main magnetic field. The radio frequency coil assembly is tuned to the resonance frequency of the dipoles to be imaged in the main magnetic field. For example, for protons in a 0.23 T field, the coil assembly is designed for optimal performance at 9.8 MHZ. The precessing magnetic moment, in turn, generates a corresponding radio frequency magnetic signal as it relaxes and returns to its former state of alignment with the main magnetic field. The radio frequency magnetic resonance signal is received by the radio frequency coil assembly which is again tuned to the resonance signal. From the received signals, an image representation is reconstructed for display on a human viewable display. Spatial position is encoded with magnetic field pulses that alter resonance frequency in accordance with spatial position. With a 9.8 MHZ nominal resonance frequency, the spatial encoding pulses typically shift the resonance frequency over about 200 kHz.

Previously, imageable fiducials have been used to correlate identified points on the surface of the patient with corresponding points in an image. Typical fiducials are hollow beads filled with a proton solution, such as copper sulfate ($CuSO_4$) in an aqueous solution. In magnetic resonance imaging, the fiducials act similarly to dipoles in the subject. When subjected to the $B_0$ main magnetic field, dipoles within the aqueous solution line up, and are tipped, refocused, and otherwise perturbed by the RF pulses. The fiducials show in a final image as bright dots and are used as points of reference for navigating an image. A problem with aqueous fiducials of this sort is that the resonance frequencies of the water in the fiducial and the water in the body are too close together, i.e., substantially the same. The fiducial marks tend to strip the imaged volume of magnetization and can saturate the spins in adjacent tissues.

Local transmit/receive coils have been used to isolate the fiducials. Typically, each fiducial has its own associated coil with a set of leads. The multiplicity of lead wires increase complexity within the imaging region and increase risk of RF burns.

Electron spin resonance (ESR) fiducials have also been used. These fiducials function similarly to the proton fiducials, except that their resonant frequencies are substantially higher. This type of system requires extra hardware. Specifically, a second set of transmitting and receiving coils are added for the microwave signals along with supporting transmitters and receivers. This increases complexity and cost.

Optical systems have also been used to track optical fiducials, as well as the surface of a subject directly. Typically, a number of cameras continually track the position of passive reflectors or active light emitters located on the subject and associated instruments. Images from the multiple cameras are used to triangulate positions of the light sources. Optical navigation systems are complex and expensive, requiring precise cameras. Optical systems must be preregistered to coincide with the physical structure of the scanner and the resultant image. Additionally, the cameras must have a line of sight to the optical emitters in order to detect the emitters, which in some cases is difficult and cumbersome.

Mechanical navigators have also been used to probe the position of a subject. Such a system may include a robot arm with instrumented joints or similar devices. It is difficult to manufacture such a system out of completely non-magnetic materials so as not to interfere with the main magnetic field. In some instances, the arm obstructs access to the subject.

The present invention contemplates a new and improved fiduciary detection method and apparatus which overcomes the above referenced disadvantages and others.

SUMMARY OF THE INVENTION

In accordance with one aspect of the present invention, a plurality of fiducial markers are disposed on a subject or on an imaging accessory. The fiducials markers have a first resonance frequency. A subject is disposed in an imaging region of a main magnetic field. Magnetic resonance is excited in dipoles of the fiducials and the subject, dipoles in the subject having a second resonance frequency. Gradient magnetic fields spatially encode the magnetic resonance, spreading the first and second magnetic resonance frequencies over first and second frequency spectra, the two spectra being separated from one another. Magnetic resonance is received from the subject and the fiducials. The signals are separated based on their frequency spectra. Image representations of both the fiducials and the subject are reconstructed.

In accordance with another aspect of the present invention, a magnetic resonance imaging system is provided. A transmitter transmits radio frequency excitation pulses with a frequency spectrum that includes first and second resonance frequencies. A receiver receives magnetic resonance signals that include the first and second resonance frequencies. Radio frequency coils transmit excitation signals from the transmitter into an examination region and receive magnetic resonance signals therefrom. A gradient magnetic field generator generates gradient magnetic fields across the examination region, spreading the first and second resonance frequencies over first and second frequency spectra, respectively. Fiducial markers are attached to the subject or a medical apparatus and resonate at the first resonance frequency. A means for determining determines the locations of the fiducials.

In accordance with another aspect of the present invention, a fiducial marker includes a non-ferrous shell defining a chamber, and liquid or gel fluorine 19 contained therein.

One advantage of the present invention resides in easily and conveniently detectable fiducials.

Another advantage resides in positioning accuracy of endocavitary coils and inserted medical instruments.

Another advantage resides in separate anatomy and fiducial signals.

Another advantage is that fiducials are located and tracked without added hardware.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts. The drawings are only for purposes of illustrating a preferred embodiment and are not to be construed as limiting the invention.

DETAILED DESCRIPTION OF THE PREFERRED EMBODIMENT

Figure 1:
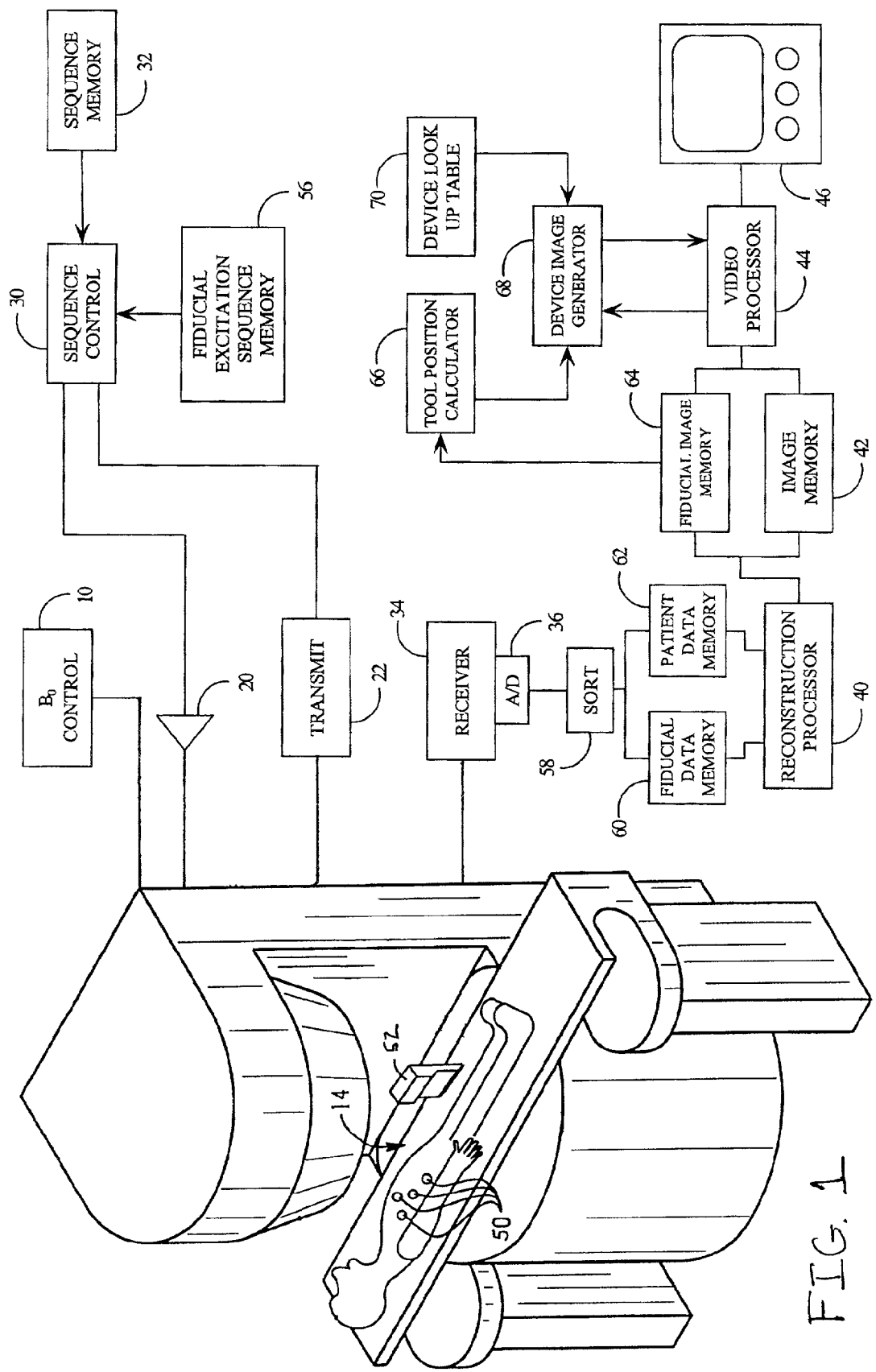
FIG. 1 is a diagrammatic illustration of an MRI scanner incorporating a plurality of fiducials, in accordance with the present invention.

With reference to FIG. 1, a main magnetic field control 10 controls superconducting or resistive magnets such that a substantially uniform, temporally constant $B_0$ main magnetic field is created along a z axis through an examination region 14. In the exemplary embodiment, the $B_0$ field is 0.23 T. A magnetic resonance generation and manipulation system applies a series of radio frequency (RF) and magnetic field gradient pulses to invert or excite magnetic spins, induce magnetic resonance, refocus magnetic resonance, manipulate magnetic resonance, spatially and otherwise encode the magnetic resonance, to saturate spin, and the like to generate magnetic resonance imaging and spectroscopy sequences. More specifically, gradient pulse amplifiers 20 apply current pulses to selected gradient coils to create magnetic field gradients along x, y, and z-axes of the examination region 14. A digital radio frequency transmitter 22 transmits radio frequency pulses or pulse packets to RF coils to transmit RF pulses into the examination region 14. In the exemplary embodiment, the transmitter is configured for an optimal frequency spectrum centered on 9.8 MHZ, and is substantially linear over a central part of the spectrum of at least 10 kHz, preferably 200 kHz or more. The spectrum includes at least 9.2 MHZ, but may suffer significant attenuation that far from the center of the spectrum. The RF pulses are used to saturate, excite resonance, invert magnetization, refocus resonance, or manipulate resonance in selected portions of the examination region 14.

A sequence control circuit 30 withdraws an appropriate sequence from a sequence memory 32, and controls the gradient pulse amplifiers 20 and the transmitter 22 to generate any of a plurality of multiple echo sequences such as echo planar imaging, echo volume imaging, gradient and spin echo imaging, fast spin echo imaging, and the like. For the selected sequence, a receiver 34 receives magnetic resonance signals from the RF coils and demodulates the signals into a plurality of data lines. If the receiver 34 is analog, an analog-to-digital converter 36 converts each data line to a digital format. Alternately, the analog-to-digital converter 36 is disposed between the radio frequency receiving coils and the receiver 34 for digital receivers. The receiver is configured to demodulate signals over a spectrum of 9–10 MHZ with peak sensitivity at 9.8 MHZ. Optionally, filters are provided to eliminate frequencies outside of the expected imaging frequencies. In the exemplary 0.23 T $B_0$ field embodiment, the filter eliminates frequencies outside of about 9.1–9.3 MHZ and 9.7–9.9 MHZ.

The data lines are reconstructed into an image representation by a reconstruction processor 40 which applies an inverse Fourier transform or other appropriate reconstruction algorithm. The image may represent a planar slice through the patient, an array of parallel planar slices, a three-dimensional volume, or the like. The image is then stored in an image memory 42 where it is selectively accessed by a video processor 44 that converts slices, projections, or other portions of the image representation into appropriate format for a display, such as a monitor 46 which provides a man-readable display of the resultant image.

For registration of the subject, a plurality of fiducials 50 are mounted to visible locations on the subject or on an instrument 52 that is to be used in the examination region. Preferably, at least three fiducials 50 are mounted in a non-linear pattern on the subject or instrument. In the preferred embodiment, with reference to FIG. 2 the fiducials 50 have non-ferromagnetic shells 54 which define a spherical cavity filled with a liquid or gel compound that includes a $Fl^{19}$ fluorine isotope. The spin lattice relaxation time of the Fluorine in the compound is preferably given a suitably small value (typically a few tens of milliseconds) by adding a paramagnetic substance to it, e.g. a small amount of $CuSO_4$ or $MnCl$. At 0.23 T, the resonant frequency of Fluorine is about 9.2 MHZ; and the proton resonant frequency is about 9.8 MHZ. This represents a difference of about six percent between the two frequencies. The difference is great enough that the signals of resonating protons and resonating Fluorine can be differentiated. The resonance frequencies are sufficiently close that the same transmitter, receiver, and coils can be used to excite and receive the resonant signals of both resonating protons and resonating Fluorine. Alternately, a doubly tuned coil is tuned to both resonant frequencies. In higher field scanners, the frequency spread between the resonant frequencies of Fluorine and protons is larger, but still only 6% different.

The reconstructed images of the individual fiducials are preferably distinguishable. In the preferred embodiment, at least one fiducial is larger than another of the fiducials for size-based differentiation. A size difference of 30% to 50% is preferred because that magnitude of size difference is readily detectable in a magnetic resonance image. The size difference allows one looking at a reconstructed image of the fiducials to orient the image in reference to a priori knowledge of a positioning of the fiducials. For instance, when three fiducials are mounted on an instrument, the differently sized fiducial can be mounted closest to the insertion end of the instrument. A priori knowledge of the fiducial spacing, nearby anatomy, and the like can also be used to determine orientation. Alternately, the hollow cavities of the fiducials can have different shapes, such as crosses, cubes, and the like. Care should be taken to select shapes that remain unique and differentiable when projection images are taken along any direction.

After the fiducials are affixed to the subject, an imaging sequence is initiated. The sequence controller 30 draws a selected sequence from an excitation sequence memory 56 to induce resonance. The resonance signals are received by the receiver 34, and sorted 58 by frequency spectra into a fiducial data memory 60 and a subject data memory 62. Because the resonance signals are spatially encoded by frequency and because the center frequencies of the fluorine and proton resonance spectra are shifted, the reconstruction processor 40 reconstructs the fiducial and proton images separately. Optionally, a frequency shift can be added to the fluorine signals to compensate for the difference in resonance frequencies.

The fiducial data is reconstructed by the reconstruction processor 40 and stored in a fiducial image memory 64. The images of the subject stored in the image memory 42 can be overlaid or otherwise combined by the video processor 44 to produce a single image showing the position of the fiducials relative to selected portions of imaged anatomy.

The combined image is then used to guide the surgical accessory 52, such as a biopsy needle or a surgical scalpel, relative to the subject. In the preferred embodiment, the surgical accessory is also instrumented with fiducials 50. As the surgical accessory is moved, additional imaging procedures are conducted. Optionally, the imaging procedures are two-dimensional projection images for greater speed. From the position of the instrument fiducials in the reconstructed fiducial image in the fiducial image memory 64, a tool position calculator 66 calculates the orientation and spatial location relative to the patient image of the surgical accessory 52. For example, the position calculator can monitor two or more fiducials of a first size that are in a known relationship (e.g., aligned with) to an axis of the surgical accessory to identify its orientation. Another identifiable fiducial or spacing among three or more fiducials can be monitored to determine which way the instrument is facing or oriented along the axis. Similar monitoring of off-axis fiducials indicates rotational orientation of the accessory. Finally, identifying a "center of mass," of the imaged fiducials indicates a location of a corresponding point on the accessory along the identified axis. Of course, other positioning algorithms are also contemplated. The axis, orientation, rotation, and position information address a device image generator 68 that generates a correspondingly oriented phantom image of an accessory based on accessory picture information from a device look-up table 70. The video processor superimposes the appropriately oriented phantom of the object on the patient image that shows the anatomy of the subject.

In another preferred embodiment, the fiducials are used to register the MR image to a radiation therapy device, and to a workstation used for simulating such a therapy. In this case the fiducials are placed on suitable places of the patient, typically flanking the center of the region that will be treated by radiation therapy. The placement is facilitated by the use of horizontal and vertical laser beams projected on the patient at or close to the desired application points. The fiducial points are marked on the patient and later used for positioning the patient into a device for applying radiation therapy, preferably using a similar set of laser beams. In this fashion, the coordinate systems of the imager and the radiation treatment device can each be made to register with the same patient coordinates. The radiation pattern of the therapy device is determined with the aid of a simulation workstation, which performs a simulation calculation in three dimensions to determine the settings and effect of the therapy device. The simulation employs a set of 3D magnetic resonance images as the input for the calculation, using the fiducial positions to fix the coordinate system.

The present embodiment can be automatically performed, and with a precision possibly better than the image resolution. For example, if a multislice image set is used, the precision in the slice direction can be made better than the slice separation. The fact that the fiducial positions are automatically determined in three dimensions can also be used to facilitate the use of two sets of three dimensional images corresponding to different patient positions in the imager. This can be convenient if the patient is so big that the fiducials do not all show in one image set. By moving the patient couch by, e.g., 20 cm. in some known direction the missing fiducial(s) can be brought into the picture. The simulation workstation can in this fashion get the missing information to piece together a complete set of images.

Figure 2:
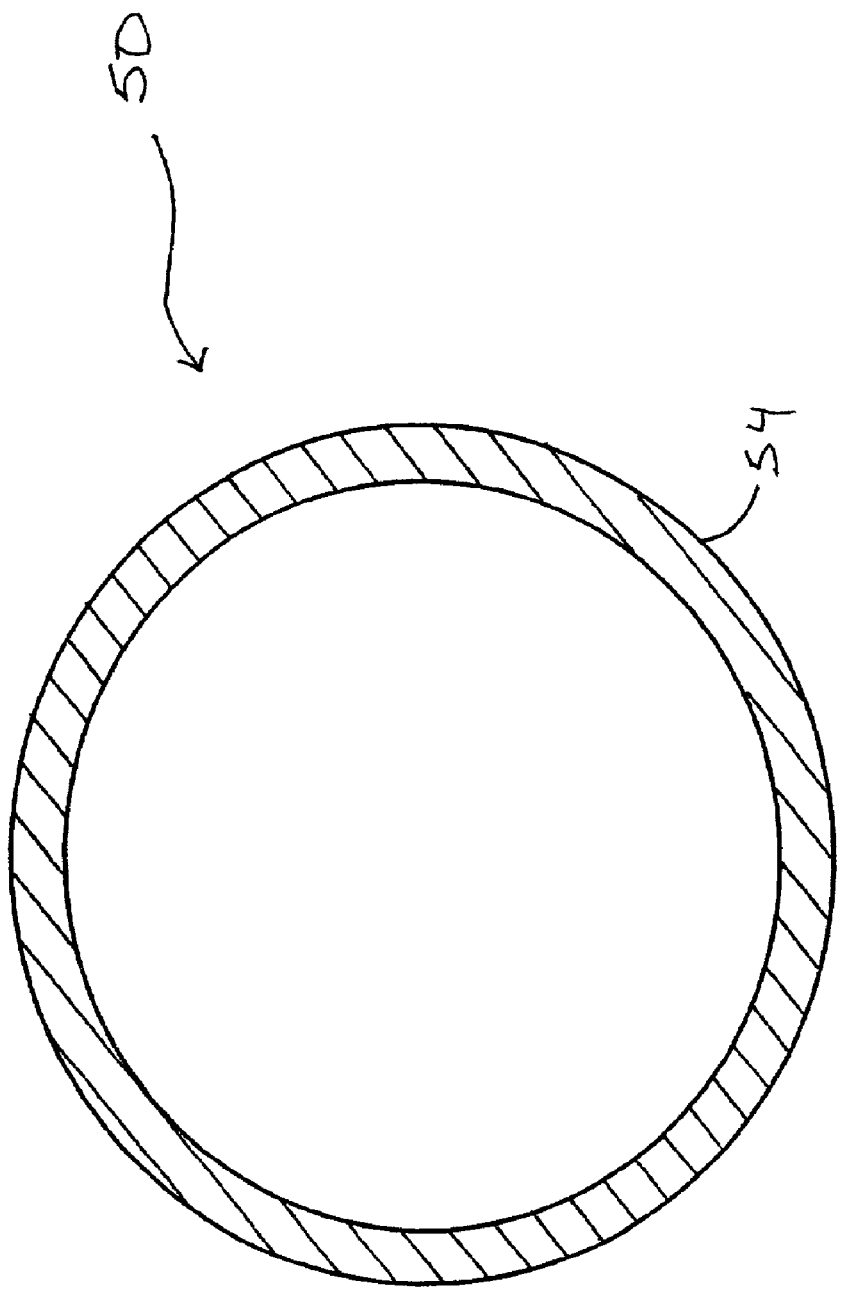
FIG. 2 is a cross sectional image of an exemplary fiducial.
Figure 3:
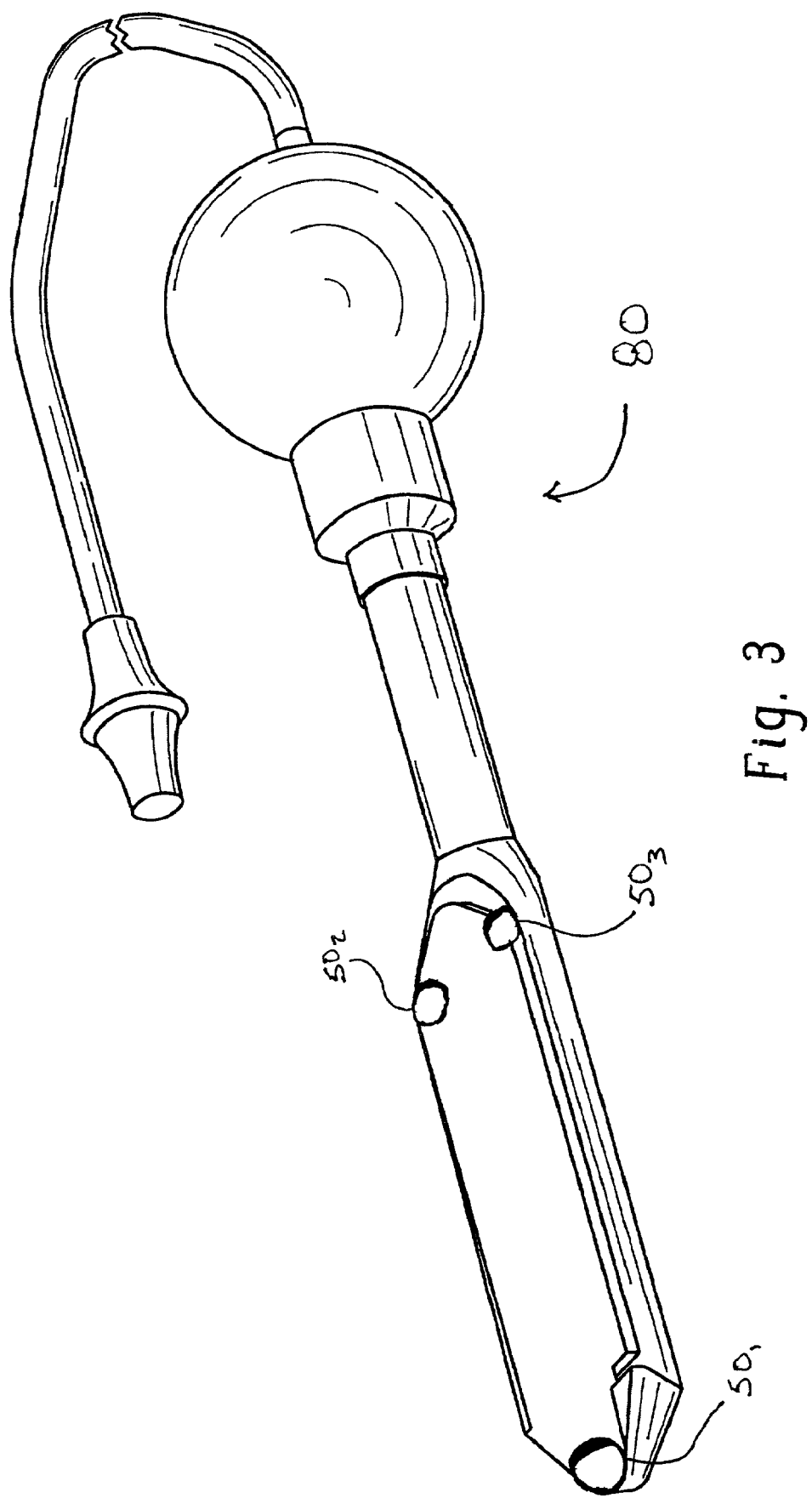
FIG. 3 is an illustration of an endocavitary probe that includes MRI sensitive fiducials, in accordance with the present invention.

In yet another preferred embodiment, as illustrated in FIG. 3, a local MRI receive coil probe 80 has a number of fiducials 50 affixed thereto. In the illustrated example, the probe is an endocavitary probe such as a rectal probe for examining the prostate. However, other insertable and surface coils can be instrumented analogously. A preferred placement of the fiducials 50 on the probe 80 is illustrated in FIG. 2, that is, a first fiducial $50_1$ at a distal end of the probe, and second and third fiducials $50_2$ and $50_3$ respectively, at lateral extremities of the probe 80. The preferred placement of the fiducials 50 allows a diagnostician to identify the position of the probe in reference to the subject and the anatomy of interest. Of course, because the dimensions of the probe are known and the locations of the fiducials is fixed, the fiducials can be mounted in a wide variety of known locations on the probe.

Another preferred embodiment is based on the fact that the set of fiducials represents a simple, a priori known configuration. Desired additional information, which includes coordinates (x, y, and z) and angular directions of the set as a whole can be acquired using an imaging sequence having a smaller number of excitations than one used to create an image, e.g., an anatomic sequence of the proton dipoles. Consequently, the time required for determining the position of the set of fiducials is only a small fraction of the time required for forming an anatomic image. Therefore, the fiducials can be beneficially utilized for automatically setting the sequence parameters for subsequent proton images to ensure that the images are oriented correctly. For example, the anatomical image may be oriented to include the surgical tool, the region just in front of the tool to aid in its insertion, and the like.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of magnetic resonance comprising:
   disposing a plurality of fiducial markers on at least one of a subject and a medical accessory, the fiducial markers including dipoles having a first resonance frequency different from a proton resonance frequency;
   disposing a subject in an imaging region of a main magnetic field;
   exciting magnetic resonance in both dipoles of the fiducial markers and dipoles in at least a portion of the subject concurrently with common radio frequency pulses, the dipoles of the subject having a second resonance frequency that is the proton resonance frequency;
   spatially encoding the magnetic resonance with magnetic field gradients which spread the first and second resonance frequencies over spatially dependent first and second frequency spectra, the first and second spectra being separated from each other;
concurrently receiving magnetic resonance signals from resonating dipoles of the subject and the fiducial markers;
separating the magnetic resonance signals based on frequency spectra;
separately reconstructing:
an image representation of the fiducial markers from the first spectra resonance signals; and,
an image representation of the at least a portion of the subject from the second spectra resonance signals.

2. A method of magnetic resonance comprising:
disposing a plurality of fiducial markers on at least one of a subject and a medical accessory, the fiducial markers including dipoles having a first resonance frequency;
disposing a subject in an imaging region of a main magnetic field, dipoles of the subject having a second resonance frequency;
concurrently exciting magnetic resonance at the first and second resonance frequencies using the same radio frequency transmitter and RF coils;
spatially encoding the magnetic resonance with magnetic field gradients which spread the first and second resonance frequencies over spatially dependent first and second frequency spectra, the first and second spectra being separated from each other;
concurrently receiving the first and second resonance signals using the same RF coil and receiver;
separating the magnetic resonance signals based on frequency spectra;
reconstructing an image representation of the fiducial markers from the first spectra resonance signals; and,
reconstructing an image representation of the at least a portion of the subject from the second spectra resonance signals.

3. The method as set forth in claim 2, further including:
calculating positions of the plurality of fiducial markers; and,
calculating an orientation of a tool on which the plurality of fiducial markers are mounted.

4. The method as set forth in claim 2, wherein:
the fiducials include fluorine 19 and the first resonance frequency is a resonance frequency of fluorine 19; and
the second resonance frequency is a resonance frequency of protons.

5. The method as set forth in claim 4 wherein the main magnetic field is 0.23 T, the first resonance frequency is about 9.2 MHZ, the second resonance frequency is about 9.8 MHZ, and the first and second spectra each span about 200 kHz.

6. The method as set forth in claim 2, wherein the fiducials are attached to the medical accessory and further including:
determining a location and orientation of the medical accessory from the fiducial marker image representation.

7. The method as set forth in claim 6 further including:
retrieving an image representation of the medical accessory in the determined location and orientation; and,
superimposing an image of the medical accessory on the reconstructed image representation of the portion of the subject.

8. The method as set forth in claim 7 further including:
as the medical accessory is moved, generating a plurality of two-dimensional projection images of the fiducials; and
updating a location of the projection image of the accessory on the subject image as the medical accessory is moved.

9. The method as set forth in claim 2, wherein the fiducial marker dipoles include fluorine 19.

10. The method as set forth in claim 9 wherein the fluorine 19 is in one of a liquid and gel form.

11. The method as set forth in claim 2, further including:
superimposing an image representation of the fiducial markers onto the image representation of the subject.

* * * * *